(12) United States Patent
Bentsur et al.

(10) Patent No.: US 11,715,082 B2
(45) Date of Patent: Aug. 1, 2023

(54) SHOPPING CART AND SYSTEM

(71) Applicant: Cust2mate Ltd., Yavne (IL)

(72) Inventors: Joseph Bentsur, Yavne (IL); Amnon Peleg, Rishon Letzion (IL)

(73) Assignee: CUST2MATE LTD., Yavne (IL)

( * ) Notice: Subject to any disclaimer, the term of this patent is extended or adjusted under 35 U.S.C. 154(b) by 0 days.

(21) Appl. No.: 17/134,002

(22) Filed: Dec. 24, 2020

(65) Prior Publication Data

US 2021/0117950 A1 Apr. 22, 2021

Related U.S. Application Data

(63) Continuation-in-part of application No. 16/174,965, filed on Oct. 30, 2018, now abandoned, which is a (Continued)

(30) Foreign Application Priority Data

Jul. 16, 2014 (GB) ..................................... 1412666

(51) Int. Cl.
*G06Q 20/20* (2012.01)
*G06Q 20/40* (2012.01)
(Continued)

(52) U.S. Cl.
CPC ........... *G06Q 20/208* (2013.01); *B62B 3/008* (2013.01); *B62B 5/00* (2013.01); *B62B 5/0096* (2013.01);
(Continued)

(58) Field of Classification Search
CPC .. G06Q 20/208; G06Q 20/201; G06Q 20/204; G06Q 20/206; G06Q 20/3223;
(Continued)

(56) References Cited

U.S. PATENT DOCUMENTS 4,071,740 A 1/1978 Gogulski
4,929,819 A 5/1990 Collins, Jr.
(Continued)

FOREIGN PATENT DOCUMENTS

CN 102708489 A 10/2012
CN 102708489 U 10/2012
(Continued)

OTHER PUBLICATIONS

See understanding/definition of being connected "serially" or in serial communication, as disclosed in the NPL document cited. See Atmel AVR, Microcontrollers (Sep. 21, 2013). Serial Communication—RS232 Basics, retrieved Mar. 20, 2021.
(Continued)

*Primary Examiner* — Peter Ludwig
(74) *Attorney, Agent, or Firm* — The Roy Gross Law Firm, LLC; Roy Gross

(57) ABSTRACT

A shopping cart and method of autonomous shopping are provided including a cart chassis, a scale configured to rest on base of the chassis, a basket resting on the scale, wherein weights of products placed in the basket are indicated by the output signal of the scale, a weight guard rail positioned above the product basket and attached to the cart chassis, a user identification unit, a payment module, and a motion sensor.

17 Claims, 7 Drawing Sheets

Related U.S. Application Data continuation-in-part of application No. 14/598,739, filed on Jan. 16, 2015, now abandoned.

(60) Provisional application No. 61/929,305, filed on Jan. 20, 2014.

(51) Int. Cl.

| | |
|---|---|
| *G06Q 20/34* | (2012.01) |
| *G06Q 40/02* | (2023.01) |
| *G06Q 20/32* | (2012.01) |
| *G06Q 30/0601* | (2023.01) |
| *G06K 7/14* | (2006.01) |
| *G06K 7/10* | (2006.01) |
| *G16H 20/60* | (2018.01) |
| *G06F 21/30* | (2013.01) |
| *G01G 19/08* | (2006.01) |
| *G01P 13/00* | (2006.01) |
| *G01C 21/20* | (2006.01) |
| *G01G 19/414* | (2006.01) |
| *B62B 3/00* | (2006.01) |
| *B62B 5/00* | (2006.01) |

(52) U.S. Cl.
CPC .......... *G01C 21/206* (2013.01); *G01G 19/08* (2013.01); *G01G 19/4144* (2013.01); *G01P 13/00* (2013.01); *G06F 21/30* (2013.01); *G06K 7/10297* (2013.01); *G06K 7/1413* (2013.01); *G06K 7/1417* (2013.01); *G06Q 20/201* (2013.01); *G06Q 20/204* (2013.01); *G06Q 20/206* (2013.01); *G06Q 20/326* (2020.05); *G06Q 20/3223* (2013.01); *G06Q 20/34* (2013.01); *G06Q 20/4014* (2013.01); *G06Q 30/0623* (2013.01); *G06Q 40/02* (2013.01); *G16H 20/60* (2018.01); *G06K 2007/10504* (2013.01)

(58) Field of Classification Search
CPC .. G06Q 20/326; G06Q 20/34; G06Q 20/4014; G06Q 30/0623; G06Q 40/02; B62B 3/008; B62B 5/00; B62B 5/0096; B62B 3/1416; B62B 3/1424; B62B 3/1428; B62B 2203/50; B62B 5/061; G01C 21/206; G01C 21/1656; G01G 19/08; G01G 19/4144; G01P 13/00; G06F 21/30; G06F 21/31; G06K 7/10297; G06K 7/1413; G06K 7/1417; G06K 2007/10504; G16H 20/60; G07G 1/0081
See application file for complete search history.

(56) References Cited

U.S. PATENT DOCUMENTS

| | | | |
|---|---|---|---|
| 5,083,638 A | 1/1992 | Schneider | |
| 5,287,266 A | 2/1994 | Malec et al. | |
| 5,734,839 A | 3/1998 | Enoki et al. | |
| 5,773,954 A * | 6/1998 | VanHorn | G06K 7/10722 |
| | | | 320/137 |
| 6,910,697 B2 | 6/2005 | Varatharajah et al. | |
| 6,997,382 B1 | 2/2006 | Bhri | |
| 7,225,980 B2 | 6/2007 | Ku et al. | |
| 7,780,081 B1 | 8/2010 | Liang | |
| 7,934,647 B1 | 5/2011 | Mims et al. | |
| 8,292,169 B2 | 10/2012 | Serjeantson et al. | |
| 8,418,919 B1 | 4/2013 | Beyda | |
| 8,464,945 B2 | 6/2013 | Connelly | |
| 8,998,218 B1 | 4/2015 | Bitondo et al. | |
| 9,230,249 B1 | 1/2016 | Vora | |
| 10,308,269 B2 | 6/2019 | Bacallao et al. | |
| 10,339,515 B1 | 7/2019 | Johnson | |
| 2002/0170961 A1 | 11/2002 | Dickson et al. | |
| 2003/0015585 A1 | 1/2003 | Wike, Jr. et al. | |
| 2004/0249717 A1 | 12/2004 | Shirasaki | |
| 2005/0189411 A1 | 9/2005 | Ostrowski et al. | |
| 2006/0208072 A1 | 9/2006 | Ku et al. | |
| 2008/0237339 A1 | 10/2008 | Stawar et al. | |
| 2008/0308630 A1 | 12/2008 | Bhogal et al. | |
| 2009/0125406 A1 | 5/2009 | Lewis et al. | |
| 2009/0140850 A1 | 6/2009 | Kangas et al. | |
| 2009/0145965 A1 * | 6/2009 | Davis | G07G 1/0009 |
| | | | 235/383 |
| 2009/0228363 A1 | 9/2009 | Segev | |
| 2009/0322481 A1 | 12/2009 | Marr, III | |
| 2012/0127314 A1 | 5/2012 | Clements | |
| 2012/0235817 A1 | 9/2012 | Forster | |
| 2012/0284132 A1 | 11/2012 | Kim et al. | |
| 2012/0296751 A1 | 11/2012 | Napper | |
| 2013/0080289 A1 | 3/2013 | Roy et al. | |
| 2013/0080719 A1 * | 3/2013 | Connelly | G07G 1/0036 |
| | | | 711/154 |
| 2013/0168426 A1 | 7/2013 | Zhang | |
| 2013/0226718 A1 | 8/2013 | Ascarrunz et al. | |
| 2013/0256041 A1 | 10/2013 | Collins, Jr. et al. | |
| 2013/0332322 A1 | 12/2013 | Perkins et al. | |
| 2014/0001258 A1 | 1/2014 | Chan et al. | |
| 2014/0175164 A1 | 6/2014 | Allard | |
| 2015/0025969 A1 | 1/2015 | Schroll et al. | |
| 2015/0112790 A1 | 4/2015 | Wolinsky et al. | |
| 2018/0060618 A1 | 3/2018 | Ferrer Alós | |
| 2018/0370554 A1 | 12/2018 | Raza et al. | |
| 2019/0026819 A1 | 1/2019 | Miyagi | |
| 2019/0287113 A1 | 9/2019 | Wright et al. | |
| 2019/0318417 A1 * | 10/2019 | Gumaru | G06Q 30/0635 |

FOREIGN PATENT DOCUMENTS

| | | |
|---|---|---|
| CN | 202541603 U | 11/2012 |
| CN | 202847767 U | 4/2013 |
| CN | 203268094 U | 11/2013 |
| EP | 2284062 A3 | 2/2011 |
| FR | 2746529 B1 | 9/1997 |
| GB | 2454274 A | 5/2009 |
| IE | S20100053 | 12/2011 |
| JP | H0370674 A | 3/1991 |
| WO | 200073971 | 12/2000 |
| WO | 2006085745 A1 | 8/2006 |
| WO | 2013134865 A1 | 3/2013 |
| WO | 2013153204 A1 | 10/2013 |

OTHER PUBLICATIONS

Definition: "transducer" as "any device, such as a microphone or electric motor, that converts one form of energy into another." See attached definition retrieved from www.dictionary.com, referring to Collins English Dictionary—Complete & Unabridged 2012 Digital Edition, retrieved Mar. 20, 2021.

* cited by examiner

SHOPPING CART AND SYSTEM

CROSS REFERENCE TO RELATED APPLICATIONS

The present application is a continuation-in-part of U.S. patent application Ser. No. 16/174,965, filed on Oct. 30, 2018, which is a continuation-in-part of U.S. patent application Ser. No. 14/598,739, filed on Jan. 16, 2015. The present application also claims priority from U.S. provisional patent application 61/929,305, entitled "Shopping System and Cart", filed on Jan. 20, 2014, and from UK patent application GB 1412666.8, entitled "Shopping Cart and System," filed on Jul. 16, 2014. The applications from which the present application claims priority are incorporated herein by reference.

FIELD OF THE INVENTION

The present invention relates to a shopping cart or to a collection of carts in general, and in particular to shopping or collection carts that allow shoppers to shop and pay for their purchases autonomously.

BACKGROUND OF THE INVENTION

Various types of payment facilities are known for allowing shoppers to record the products they have selected at a store and to make a payment for those products autonomously, that is, without a store clerk. Some systems include methods for comparing products selected by a shopper with products placed on a scale. However, a scale may be subject to various motions and pressures that distort a weight reading. Various improvements to autonomous shopping and in particularly to aspects of an autonomous shopping cart may increase the reliability and security of an autonomous shopping process.

SUMMARY OF THE INVENTION

The present invention provides a shopping cart or collection cart and inter-related shopping system, for enabling shoppers to shop and pay for their purchases autonomously.

In accordance with embodiments of the present invention there is provided a shopping cart that may include a cart chassis having an upright portion, a base, a handle bar attached to the upright portion, wherein wheels are attached to the base, and a scale configured to rest on the base. The scale may be configured to provide an output signal indicative of a downward pressure on the scale. Typically, the scale includes one or more weight transducers. A basket of the shopping cart may be configured to rest on the scale, such that weights of products placed in the basket are indicated by the output signal of the scale. A user identification unit may be configured to receive a form of identification from a shopper and responsively to authenticate an identification of the shopper. One or more product sensors may be configured to identify a product placed into the basket or a product placed in proximity to one of the sensors. A motion sensor may be configured to provide a motion signal to allow product weighing only when the shopping cart is stopped. A user interface may be configured with a touch screen, having an associated processor configured to receive a signal indicative of cart movement from the motion sensor and responsively to issue an alert that a product cannot be weighed while the cart is in motion. A payment module may be configured to receive a payment method from the shopper and responsively to perform a payment transaction for the products in the basket.

The motion sensor may be one of an accelerometer, an encoder configured to measure wheel rotation, or a camera configured with movement recognition.

In some embodiments, the shopping cart may be configured to issue a user indication to remove a product placed in the basket when the basket is in motion.

The one or more product sensors may include a barcode reader, an RFID reader, an NFC reader, a QR The user identification unit may be a credit card reader, a smart card reader, a biometric reader, a mobile phone application or a mobile phone sensor.

The payment module may be configured to implement a payment transaction process according to a total price of products placed in the basket, to receive a payment transaction authorization, and responsively to issue a signal of a payment confirmation to confirm that payment has been successfully received. In some embodiments, the payment transaction may be one of a credit card transaction, a mobile phone application payment, or a bank transfer. Additionally or alternatively, the payment module may include a shopping cart registry and the shopping cart registry may be configured to log a "paid" status responsively to the payment confirmation. The payment module may also be configured to transmit the shopping cart status to a user interface.

In some embodiments, the user interface includes a touch screen, configured to accept a product identification identified by the one or more product sensors or entered by the shopper, and having an associated processor configured to determine a product correspondence between the product identification and the output signal of the scale.

The user interface may be further configured to provide product information including: cost of a product; price per weight of bulk products; nutrition information; product content weight; product volume; analogous products to a selected product; a notice of whether a product may be on sale; product ingredients; and product warnings including potential allergens, gluten content, artificial sweeteners and colors. The product information may be a type of bulk commodity and wherein the processor may be further configured to determine a price according to the type of bulk commodity and the output signal of the scale. The type of commodity may be one of a type of fruit, vegetable or nut. The processor may be further configured to generate a lock release signal when a payment method is authenticated by the payment module and when a shopper is identified by the user identification unit.

In some embodiments, the shopping cart may include a locking mechanism coupled to an external charger. The locking mechanism may be configured to receive power from the external charger to charge a power supply of the shopping cart, and the locking mechanism may be further configured to receive a lock release signal from the user interface and responsively to release the shopping cart from the external charger.

A visual indicator may be positioned on the shopping cart and configured to switch on responsively to the signal of payment confirmation.

An indoor navigation system may be configured to include a map and/or voice commands for in-store navigation of the shopping cart.

The user identification module, the payment module or the user interface may be configured to receive input from a mobile phone.

Also provided by embodiments of the present invention are methods for autonomous shopping that may include: providing a shopping cart including a chassis having an upright portion, a base, a basket, a handle bar attached to the upright portion, a motion sensor, and wheels attached to the base; providing, by a scale resting on the base, an output signal indicative of a downward pressure on the scale, wherein the scale includes one or more weight transducers, such that weights of products placed in the basket are indicated by the output signal of the scale; receiving, at a user interface of the cart, from the motion sensor, a signal indicative of cart movement and responsively providing an alert to a user to stop the cart before placing a product in the basket; receiving identifying information from the shopper at a user identification unit of the cart; receiving, at a payment module of the cart, a payment method from a shopper to complete a payment transaction; identifying, by one or more product sensors, one or more products placed into the basket or in proximity to one of said product sensors; and making the payment transaction by the payment module, responsively to receiving the shopper identification, to receiving the payment method, and to identifying the one or more products.

Although the present cart and system will be described herein with respect to a supermarket environment, it should be understood that the cart and system could be implemented in a warehouse (to control inventory, prevent theft, etc.) or other appropriate settings. As such, the cart and system can be considered to provide the application of a platform for collecting and subsequently distributing products.

BRIEF DESCRIPTION OF THE DRAWINGS

The present invention will be understood and appreciated more fully from the following detailed description taken in conjunction with the appended drawings in which.

The following detailed description of embodiments of the invention refers to the accompanying drawings referred to above. Dimensions of components and features shown in the figures are chosen for convenience or clarity of presentation and are not necessarily shown to scale. Wherever possible, the same reference numbers will be used throughout the drawings and the following description to refer to the same and like parts.

DESCRIPTION OF EMBODIMENTS

Illustrative embodiments of the invention are described below. In the interest of clarity, not all features/components of an actual implementation are necessarily described. Embodiments and/or limitations featured in the figures are chosen for convenience or clarity of presentation and are not meant to limit the scope of the invention.

Figure 1:
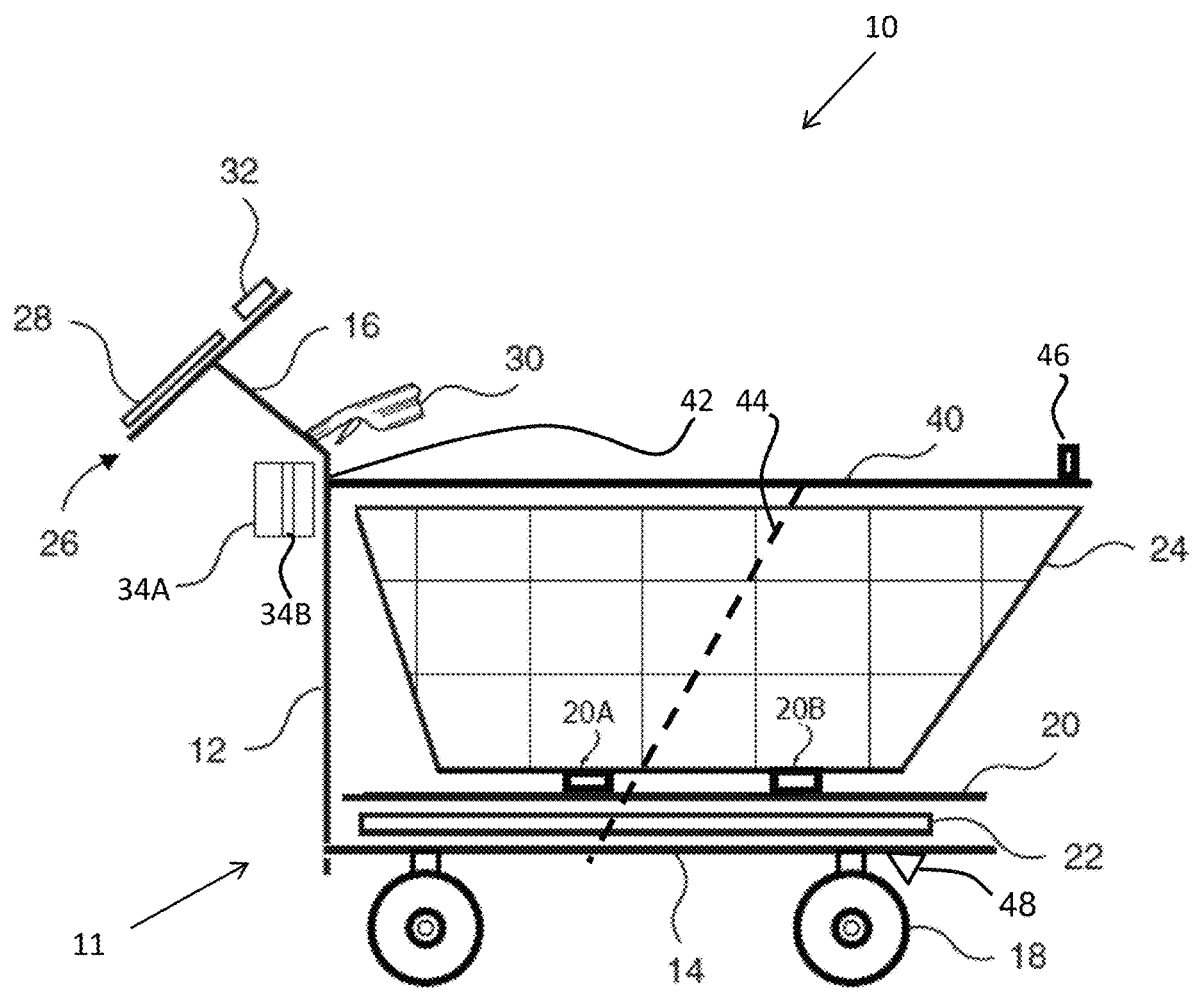
FIG. 1 is a schematic side view of a shopping cart for autonomous payment, in accordance with embodiments of the present invention.

FIG. 1 shows a schematic depiction of a shopping cart 10, in accordance with embodiments of the present invention. The shopping cart includes a cart chassis or platform 11, typically having an upright portion 12, a generally horizontal portion or base 14, a handle bar 16 attached to the upright portion, and wheels 18 operably attached to the base. The shopping cart also has a product scale 20, which rests on the base 14 and which typically has shock absorbers 22 supporting the scale on the base 14.

A product receiving portion or basket 24 is configured to floatingly or fixedly rest on the scale, such that products placed in the basket may be weighed. A user interface 26 typically includes a processor 32, including memory storage, and a touch screen 28, and additionally or optionally an audio interface and/or a video interface. The shopping cart includes one or more product sensors 30, such as a barcode reader, an RFID reader, a Near Field Communications (NFC) reader, and/or a camera (or image and/or video capture unit). The product sensors 30 communicate with the user interface 26. A product sensor (also referred to hereinbelow as the "sensor") may be configured to identify a product and/or to read the cost of a product or information for determining the cost, such as a label indicating a price per weight in the case of bulk products such as fruits and vegetables. The product sensor may also be configured to send product information (such as type, price, weight, name, ingredients, nutritional information and such) to the user interface 26 to store data about the product, such as content weight and/or volume, analogous products, product discounts, product ingredients, and warnings such as product contents (such as potential allergens, gluten, and artificial sweeteners or colors). User interface 26 has associated or integrated therewith the processor 32, which controls and processes interaction of the cart activities with a store's computer system and in some preferred embodiments with a server configured in an internet cloud.

In some embodiments, product sensor 30 includes image capture functionality (still image and/or video) may be configured to recognize an identification of each product based on its captured image (using image recognition techniques of the art). The recognized image may be associated by the processor with the product's shape/dimensions (which may include aspect ratio and such relative dimensions); and/or contours, and/or words and/or writing font and/or colors and/or graphics, and/or images and/or any other distinctive features on the product packaging.

In some embodiments, a first product sensor 30 is a barcode reader that identifies a product barcode and a second product sensor 30 is a camera providing image capture and a recognition module that identifies a product by its captured image. The processor 32 may be configured to confirm that the product identified by its barcode is indeed the same product recognized and identified by its image as placed in the basket 24. This verification is helpful in identifying potential fraud, for example, a user scanning a first product (for example a small package of the product) but then actually placing a different product in the basket 24 (for example, a larger package of the product).

In some embodiments, the processor 32 is configured to confirm that the product identified by its barcode is indeed the same product recognized and identified by its image as placed in the basket 24 and that the weight of the product added to the basket (as 24 transmitted by the digital output of the product scale 20) corresponds to the weight associated with the product identified by the barcode and image. The weight associated with a product added to the basket 24 is calculated by storing in memory the current weight of the basket (say 2.5 kilos) and then when a new weight reading is obtained from the product scale 20 (say 2.8 kilos), deducting the current weight reading from the previous reading and in this example deducting that 300 grams have been added to the basket 24 (could be one or more new products). The weight reading of the scales 20 can be obtained either by a pull mechanism (the user interface 26 requesting a reading periodically, say 10 times per second) and/or a push mechanism (where the scale transmits a new digital output every time there is a change is the weight measured).

Removal of a product (i.e., an item) from basket 24 also may require scanning the removed product by a product sensor 30 so that the shopper is not charged for the removed product. The processor 32 can thus be configured to subtract the cost of a removed product upon scanning, after sensing the decrease in weight of basket 24. In accordance with additional or alternative embodiments, processor 32 may be configured to automatically reduce the price of the removed product if the weight of the product is sufficiently distinct from other products. Product removal may be completely automatic or may require confirmation by the shopper via touch screen 28.

In some embodiments, the sensing of a product placed in (or removed from) basket 24 may include a comparison of the expected weight of the product with the actual change in weight indicated by scale 20. This prevents an error that may occur if two products are inserted (or removed) at the same time but only one product is scanned. The weight sensing by scale 20 ensures that products placed in basket 24 have been scanned.

The touch screen 28 may be configured to accept product information identified by the one or more sensors 30 or manually entered by a user. The processor 32 may be configured to determine a product correspondence between the identified product information and the output signal of the scale 20. The user interface 26 may be configured to provide product information on the touch screen 28. This may include: a cost of a product; a price per weight of bulk items; nutrition information; a product content weight; a product volume; a list of analogous products to a selected product; a notice of whether a product is on sale; product ingredients; and product warnings including potential allergens, gluten content, artificial sweeteners and colors. The product information may be a type of a bulk commodity. The processor may be further configured to determine a price according to the type of bulk commodity and the output signal of the scale 20. (Commodities may include fruits, vegetables, nuts, spices or other commodities sold unpackaged.)

The user interface 26 may also be connected and operated by a mobile phone and similar mobile devices, whereby an application on the mobile phone can communicate with the processor 32. Information such as shipping lists; recipes; advertisements, and so on, can thereby be communicated between the shopper and the processor 32. In addition to the touch screen 28, the interface 26 may include a microphone and/or speaker for providing and receiving information and/or instructions from the shopper.

In some embodiments, a mobile phone can provide the functionalities of the user interface 26.

In particular embodiments of the shopping cart, the scale 20 may include one or more pressure transducers 20A and 20B (also referred to as "weight transducers"), calibrated to provide an electric, analog or digital signal indicating a weight of the basket 24 itself together with the weight of products added to the basket 24. The scale 20 is in communication with user interface 26, which is configured to display weight information provided by the scale 20. The processor 32 is also configured to check that there is correspondence between the measured weight and the expected weight of a product sensed by the one or more sensors 30, thereby avoiding store pricing errors or fraud by the user. Scale 20 is configured to properly subtract the weight of basket 24 to measure the tare weight, in order to ensure proper weighing of products. Outputs of multiple transducers may be averaged by the scale to provide a single, more representative weight indication. In some embodiments, the scale 20 is configured to sense weight changes of 1, 2, 3, 4, or 5 grams.

Basket 24 may be attached to the base 11 of the cart in a manner such that the basket may freely move downward with the weight of products accumulating therein. For example, basket 24 may be loosely tethered to chassis 11 by a tether (not shown); or have rails that fit a vertical track (not shown) so as not to fix the basket 24 to the chassis 11, but rather to allow the basket 24 and its contents to be weighed by scale 20 without hindrance. The bottom of basket 24 and the top of scale 20 may be correspondingly shaped so they can be fixed to each other.

The shopping cart may also include an identification unit 34A and a payment module 34A. The identification unit 34A identifies a shopper and may be a credit card reader, a smart card reader, a biometric reader (via finger prints, face recognition, voice recognition, etc.), a mobile phone application or a mobile phone sensor. When implemented as a credit card reader, the identification unit may also include the payment module as an integral component, the payment module including the additional functions of authenticating a shopper and processing a payment transaction through a remote confirmation. The authentication process may include transmitting credit card information together with shopper identification information to a remote computing service and receiving an authentication confirmation, or alternatively a rejection of the authentication. A payment transaction may include transmitting credit card information in addition to payment details to a remote computing service and receiving a payment confirmation (or rejection).

In some embodiments, the cart further includes a guard rail 40 positioned above the product basket 24 and operably attached to the cart chassis 11, for example, at a connection point 42 with the upright portion 12. Additional rail support bars, such as support bar 44, may provide additional support to position the guard rail 40 above the upper edge of the basket 24. The guard rail 40 isolates the basket 24 from potential external forces that would affect the weight measurement. For example, a downward force on the guard rail 40 does not impose a downward force on the basket 24. Consequently, if a shopper leans on the guard rail 40, the shopper's weight is transmitted to the product basket 24 and is thus not indicated by the output signal provided by the scale 20. If the guard rail 40 were not in place above the basket 24, a shopper leaning on the basket 24 would cause erroneous measurements to be made by the scale 20, and would therefore prevent proper processing of items added to the basket 24.

In some embodiments the shopping cart includes a visual indicator 46, such as a light, which, for example, may be mounted on the guard rail 40. The visual indicator 46 may be configured to switch on after a payment confirmation is received, so that it is easily and visually clear that payment has been made for a shopping cart's contents, for example, when the user exits the store.

The user interface 26 may also be configured with a printer to provide a paper receipt, and/or, in conjunction with the payment module, to provide an electronic receipt.

The shopping cart may also include a motion detector or motion sensor 48, which may be an accelerometer, an encoder measuring wheel rotation, a camera with movement recognition, or other technologies known in the art for detecting motion. The motion sensor 48 provides a motion signal to the processor 32 indicating whether or not the cart is in motion. When it is in motion, the processor may wait until the cart is stopped before recording a weight of a new product placed in the basket, as measurements taken while the cart is in motion may be inaccurate. The processor may also issue, on the user interface, a message to the shopper that the product cannot be weighed until the cart is stopped. The message may also indicate that, for example, a product should not be placed in the cart until the cart is stopped.

Figure 2:
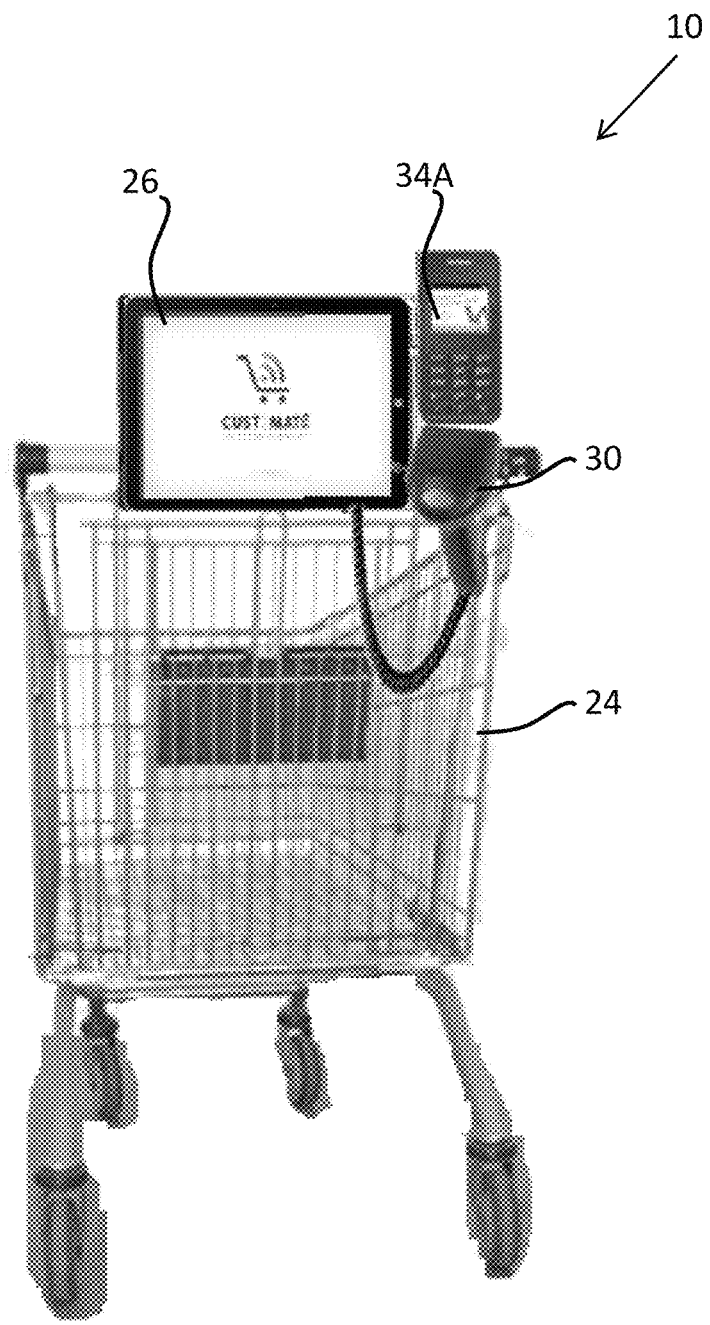
FIG. 2 is a schematic back view of a shopping cart for autonomous payment, in accordance with embodiments of the present invention.

FIG. 2 is a schematic back view of the shopping cart 10 for autonomous payment, in accordance with embodiments of the present invention. The back view shows more clearly the position of the basket 24, in relation to the user interface 26, the sensor 30, and the identification unit 30.

User interface 26, which may include, for example, a touch screen 28, in conjunction with the processor 32, can be configured to: (1) indicate the price, name, picture and weight of the products placed in basket 24; (2) provide information to the shopper about analogous products available; (3) receive information from the shopper (e.g. a shopping list) including information received from external applications or databases handling user information such as shopping lists; (4) indicate where products on the shopping list are located in the store, by providing location information (i.e. rice is on isle 7), a map of the store and/or a navigation feature or system; (5) suggest complimentary products (e.g. if lunch meat was an item, then sandwich bread might be suggested); and (6) automatically put required products of a recipe on the shopping list.

Figure 3:
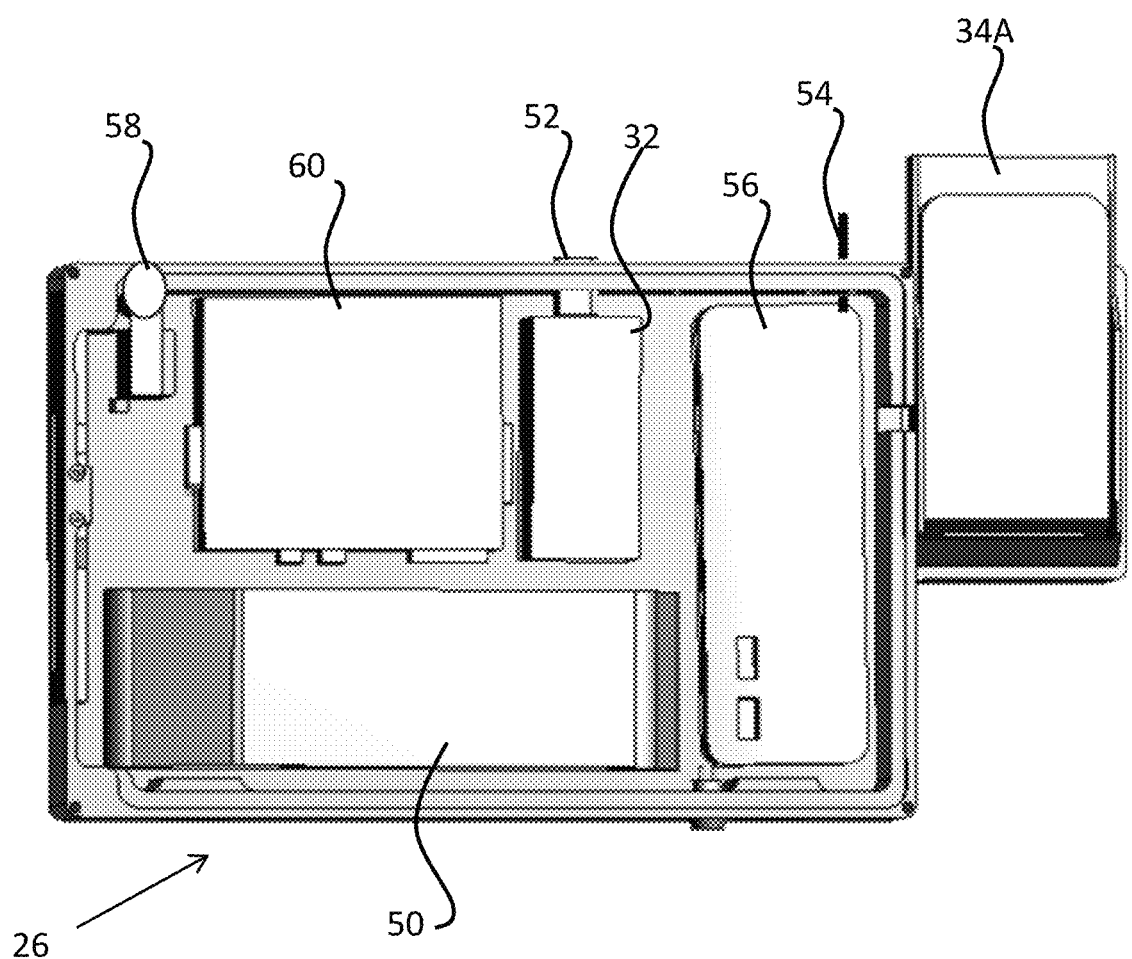
FIG. 3 is a schematic view of a user interface and identification unit of a shopping cart for autonomous payment, in accordance with embodiments of the present invention.

FIG. 3 is a schematic view of the back sides of the user interface 26 and the identification unit 34A of a shopping cart for autonomous payment, in accordance with embodiments of the present invention. Components of the user interface 26 may include the processor 32, as well as a battery 50, and a transducer connector 52 for receiving transducer signals of the scale 20. In some embodiments, the interface 26 further includes a Wi-Fi transmitter 56 and antenna 54 for wirelessly transmitting information between the processor and a store's computer system, such as the weight and identification of products added to the basket 24.

The characteristic weight and the barcode data of each product, for example, may be wirelessly transmitted to/from the processor 32 to/from the shop's/store's computer system, for example via a Wi-Fi connection provided by transmitter 56.

The user interface 26 may also communicate with a locking mechanism 58, which may be coupled to an external charger. The locking mechanism 58 is configured to receive power from the external charger via a charging cable to charge the battery 50 (also referred to herein as the interface power supply). When the charging cable is inserted to the locking mechanism 58, it both charges the battery 50 and prevents free movement of the shopping cart. The locking mechanism 58 is configured to receive a lock release signal from the processor 32 and responsively to release the charging cable from the locking mechanism 58. The processor 32 may be configured to generate a lock release signal when a payment method is authenticated by the payment module and/or when a shopper is identified by the user identification unit.

Alternatively, the shopping cart may be mechanically and electrically connected to additional shopping cart or carts in shopping cart zone (where users release and return carts).

In some embodiments, the user is charged a predetermined amount if the shopping cart is not correctly returned to the shopping cart zone.

The user interface 26 may also include additional circuitry 60, which may include components for additional electronic, audio, or visual signal generation, (in addition to the touch screen) such as generation of an alarm if a product identification error occurs, as described below. In some embodiments, the processor 32 is configured to provide an alarm/warning (audio or other) that the product has not been properly scanned by product sensor 30 upon sensing that the weight in basket 24 has increased. Circuitry 60 may also include location sensing circuitry, such as GPS circuitry. The GPS circuitry may transmit location information to a store computer, for example for locating the cart if it is not properly returned to a shopping cart station.

A navigation feature of the interface may include a store directory, a map and/or voice commands, providing the shortest path to arrive to the product location. In particular embodiments, the navigation feature additionally or alternatively uses imaging (image processing, for example by the processor 32) of the store plan (floor plan/layout) and/or the specific environment/location to provide navigation information to the shopper. The imaging feature can be configured to identify the goods in the purchaser's vicinity, which may thereby be used to provide purchasing information to the user, for example if any such products are on sale and/or a quality report on products in the area, and so on. In some embodiments, the aforementioned image processing is used in conjunction with the store's system to identify the location of the shopper, which can be used for navigation and to promote purchasing, for example, by suggesting newly offered products in the vicinity. Wheels 18 may also be motorized and controlled by the processor to navigate according to the map.

As described above, the user interface 26, with support from the processor 32, may further be configured to receive information (e.g. a shopping list or recipe), for example, from a smartphone application, a website or the like, so the shopper does not need to input a shopping list on the spot, but rather can make the list when convenient, to avoid forgetting desired products and save time in the store. The smartphone application could be programmed to provide information on upcoming sales; new products that have recently come out; and to suggest products based on learned shopping patterns. Further, in some embodiments, the application may allow multiple members of a group, e.g. a family, to separately access and update their shopping list, each one independently from his/her own smartphone.

An exit gate may be configured to sense if payment has been made. Such a feature of the system can be embodied by a scanner of the type used in airport security, which can provide an alarm in the case of any issues and/or control an exit gate.

The shopping cart may also include a camera configured to identify a shopper and/or used to identify anyone stealing the shopping cart. The camera is configured to provide a live video stream to the store's computer system or alternatively to an internet application.

In some embodiments, the shopping cart includes a shopping bag dispenser (not shown) whereby packaging of products can be performed conveniently by the customer. In some embodiments, bags or cartons are prearranged in the cart.

A system supporting the shopping cart may include an entrance gate or entry system configured to register the cart and electronically match the cart with the shopper. The gate may read identifying information transmitted from the cart and, upon identification of the shopper, for example via the payment module 34, such as a credit card reader, the gate may match the cart with the shopper. This matching capability may alternatively or additionally be provided by the user interface. Matching prevents cart switching or theft. The cart registration match with the shopper can be verified at an exit gate system, as described in more detail below.

As a shopping cart leaves a store, an exit gate system, including, for example, a gatekeeper device similar in design to an airport security gate, may verify that payment has been made and may verify the weight of the corresponding purchases corresponds. The exit gate system then opens allowing the shopper to exit the store and bring the cart to the shopper's vehicle, if any, and then to a cart collection point or padlock (also referred to herein as the shopping cart station) where the shopping cart is placed and preferably mechanically and electrically connected to the collection point or connected to a cart already located in the collection padlock. In this manner, the carts can be electrically charged for further use. Upon returning the cart, the shopper is "disconnected" from the system.

In addition to the exit gate system ensuring the cart belongs to a shopper who registered it (who took the cart), typically using an electronic sensor, the exit gate system may also verify that payment was made via the cart, that the weight and products correlate; and that a payment receipt was generated, prior to opening a gate or automatic door.

Figure 4:
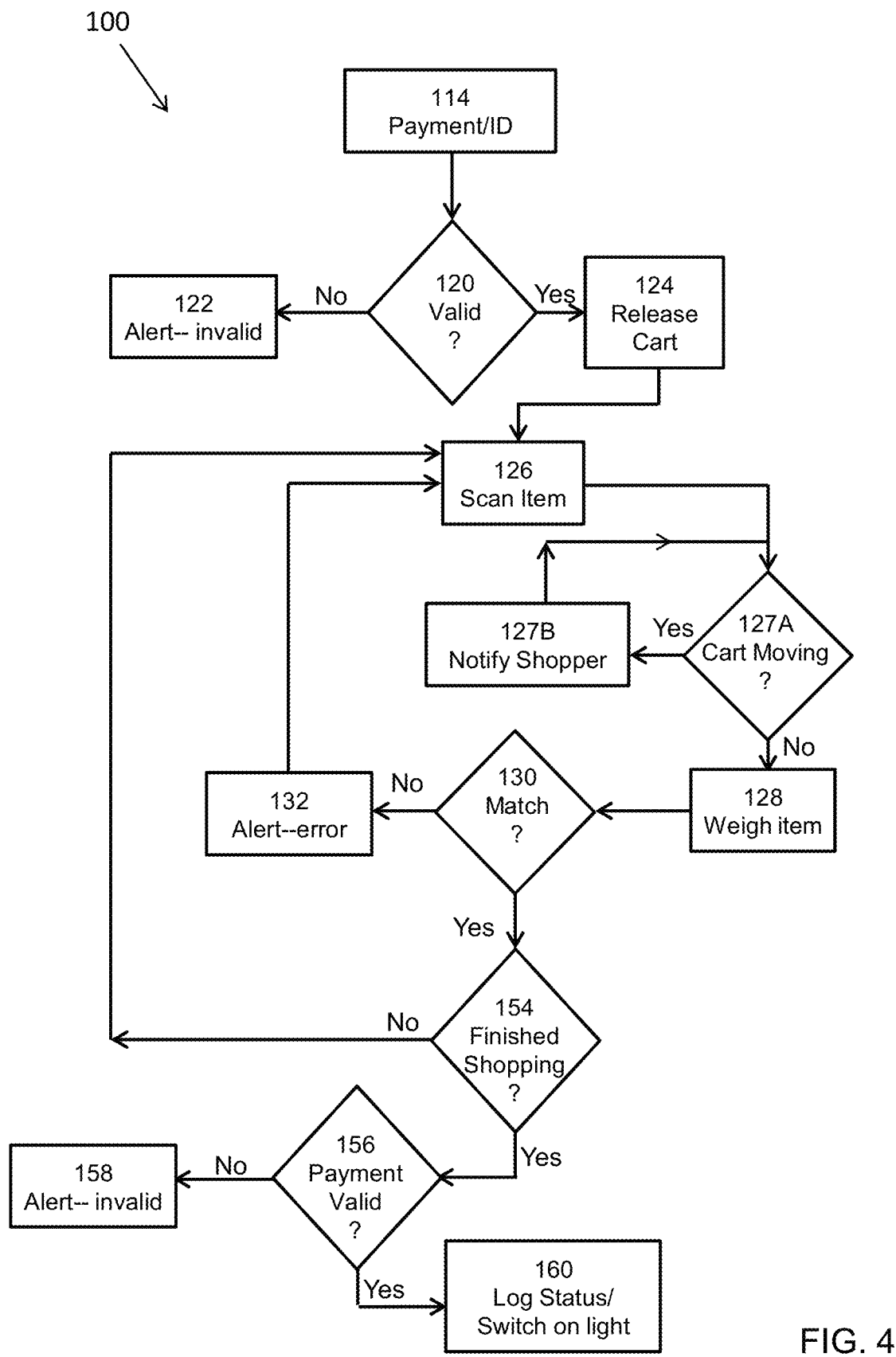
FIG. 4 is a flow diagram of a process of shopping with autonomous payment, in accordance with embodiments of the present invention.

FIG. 4 is a flow diagram of a process 100 of shopping with autonomous payment, in accordance with embodiments of the present invention. At an initial step 114, a shopper selects a shopping cart by providing a form of identification (such as a password, an identifying card, or a biometric input) to an input device of the locking mechanism and/or a means of payment. This is validated at a step 120. If not valid, an alert to the shopper is provided at a step 122; otherwise the locking mechanism releases the cart at a step 124, as described above.

At a step 126, the shopper scans a product, the bar code or image of the product being received by the processor as described above. In some embodiments, the shopping cart is designed to reduce weighing errors that may be caused by cart movement. The processor may be configured to receive signals from the motion sensor and to confirm that the cart is not moving at a step 127a, so that the product, when placed in the basket, may be weighed accurately. If the cart is moving, the processor may issue a notification (i.e., an error alert) through the user interface at a step 127b that the shopper must stop the cart before a product can added to the cart and weighed. The notification may also indicate that a product added to the basket while the cart is in motion should be removed and place in the basket again when the cart is stopped. Once the cart has stopped, the user may then be instructed to place the product in the basket at a step 128. That is, the processor may be configured to issue an error alert at the user interface whenever a product is placed in the basket when a cart is moving.

After each product is scanned and placed, the processor determines at a step 130 if the identification matches the weight. If not, at a step 132, an alert is provided to the shopper (at the user interface). If there is a match, shopping may continue. The product is also recorded by the processor 32 for subsequent generation of a bill for payment. At a step 154, if the shopper has not finished, he continues to scan and place new products in the basket. If finished, at a step 156, the payment module receives from the processor the total price of items in the basket, receives a payment instruction from the shopper, and performs a payment transaction. If the transaction is not successful, an alert (issued typically at the user interface) is made at a step 158. If successful, the success is logged at a step 160, and additional measures as described above are taken to confirm the transaction, such as lighting the visual indicator and recording the transaction confirmation in the processor registry.

Figure 5:
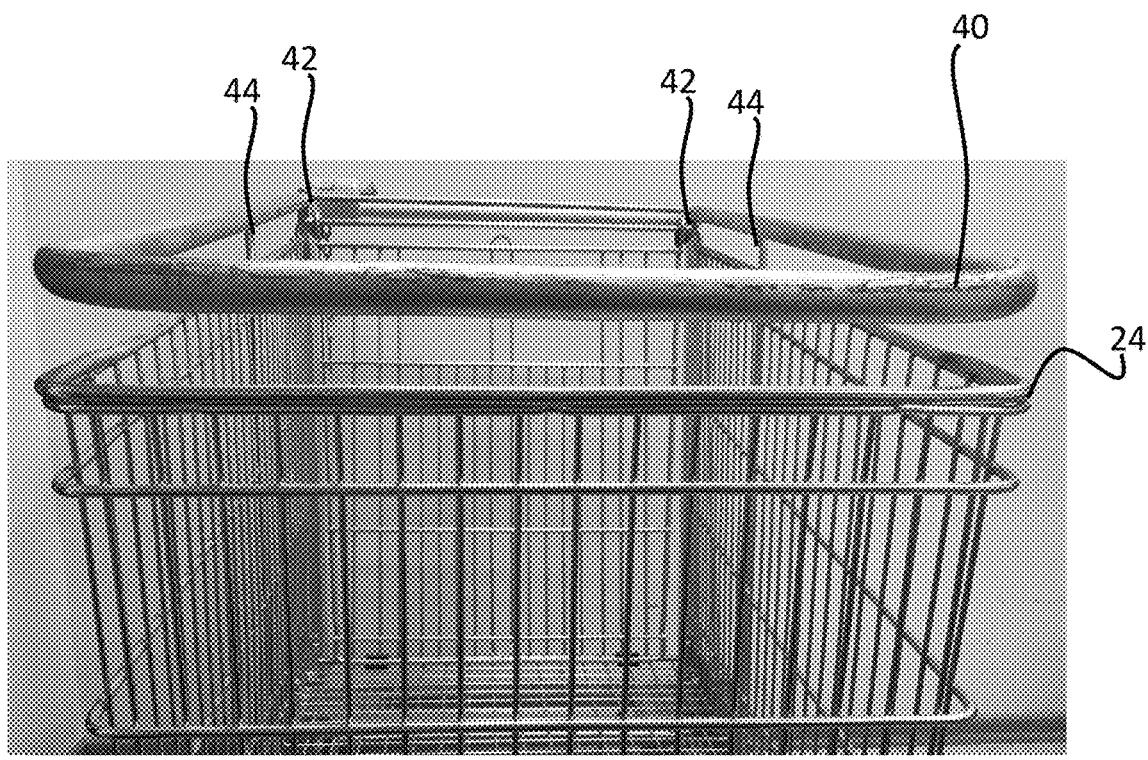
FIGS. 5-7 are photographs of a shopping cart for autonomous payment with a guard rail, in accordance with embodiments of the present invention.
Figure 6:
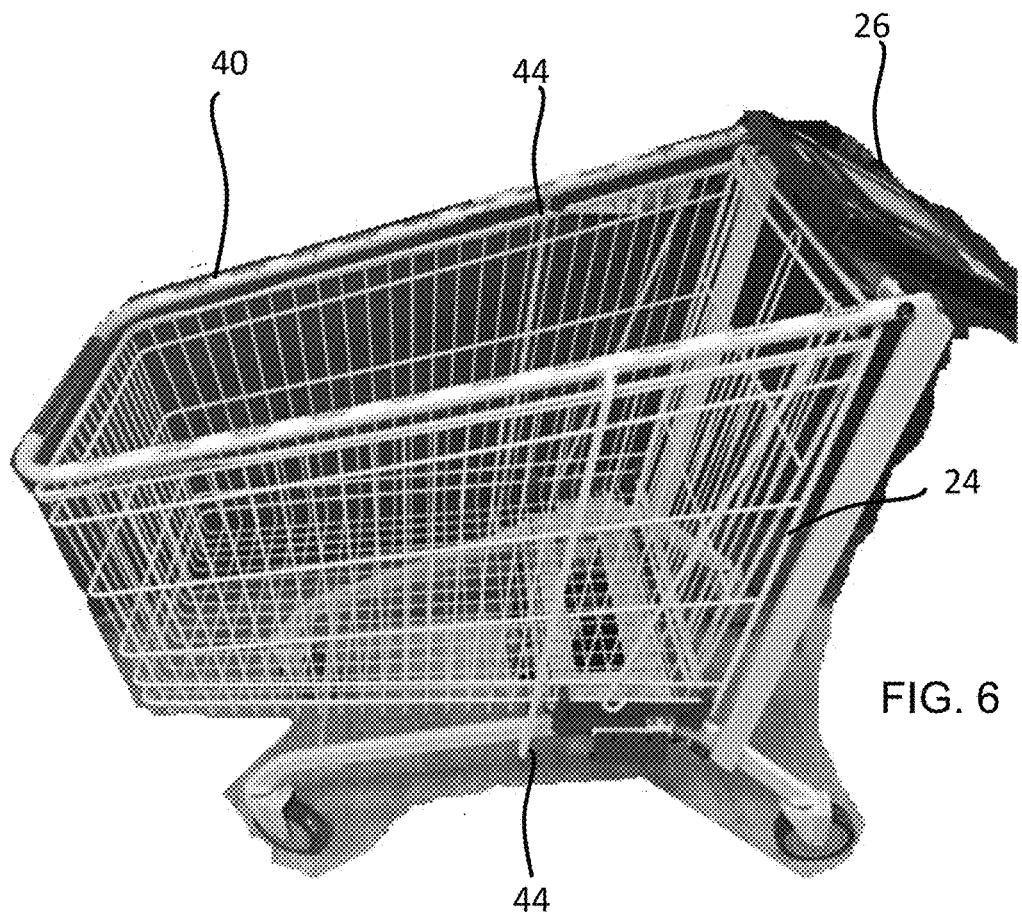
Figure 7:
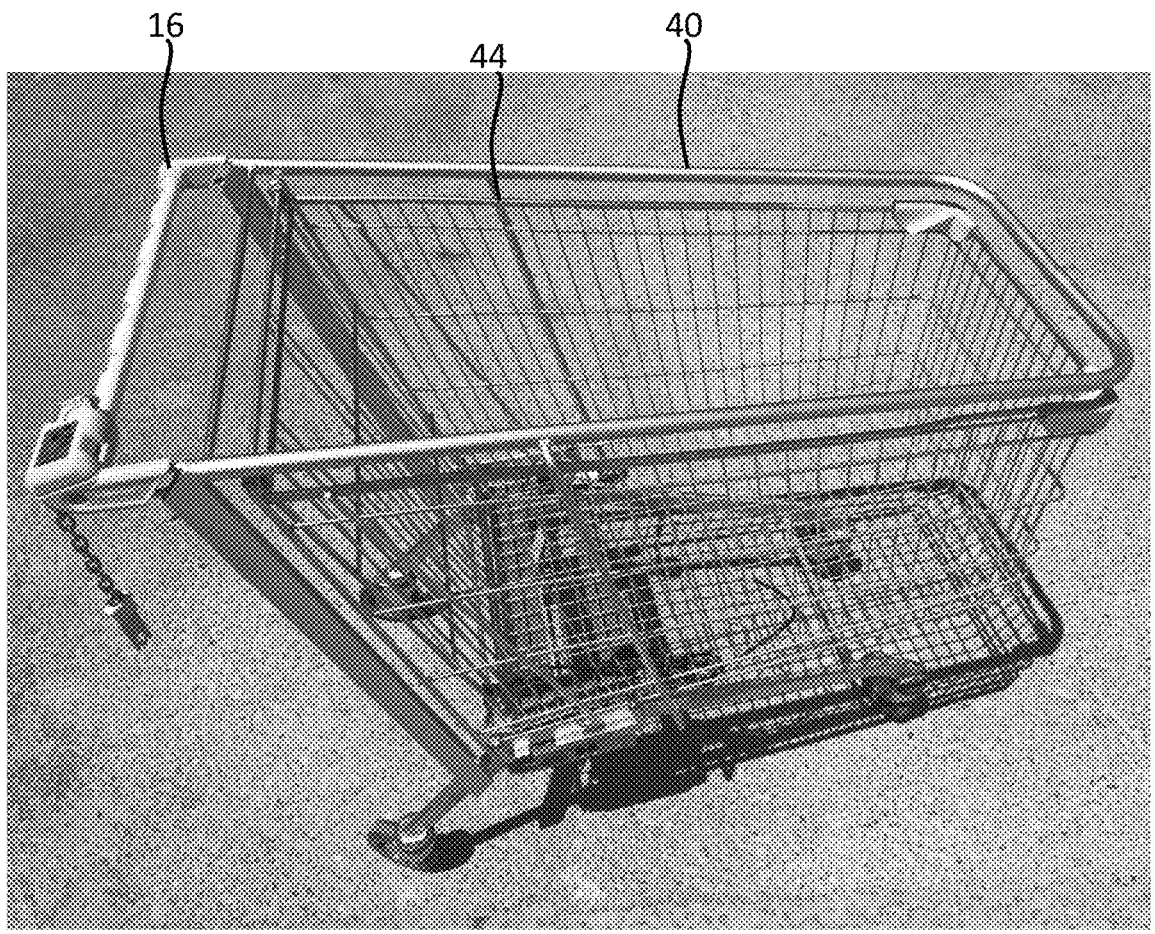

FIGS. 5-7 are photographs of the shopping cart 10 for autonomous payment with a guard rail 40, in accordance with embodiments of the present invention. The photographs show the guard rail 40 protecting the basket 24, so that when someone presses down on the cart, from above the top edge of the basket, the pressure is imposed on the guard rail 40, rather than on the basket. FIG. 5 shows a front view of the basket, showing the guard rail 40 connected to the cart chassis 11 at the connecting points 42 and by means of the support bars 44. The basket 24 and the guard rail 40 are shown in FIG. 6 in relation to the user interface 26, and in FIG. 7 in relation to the cart handle 16. As indicated, the guard rail may protect the top edge of the basket on both the left and right sides of the basket as well as at the front of the basket.

In some embodiments, the support bars 44 extend vertically below the guard rail 40 and thus adding the support bars 44 does not affect the overall width of the shopping cart.

In some embodiments as can be seen in FIGS. 6, 7, the support bars 44 extend first horizontally from the guard rail 40 (towards the outside of the shopping cart) before descending vertically to connect to the base 14 and thus adding the support bars 44 increases the overall width of the shopping cart. In these embodiments, the outside extension of the support bars 44 may be helpful when pushing one shopping cart inside another shopping cart, typically to save in space in a shopping cart service area where shoppers obtain and return shopping carts.

Figure 8:
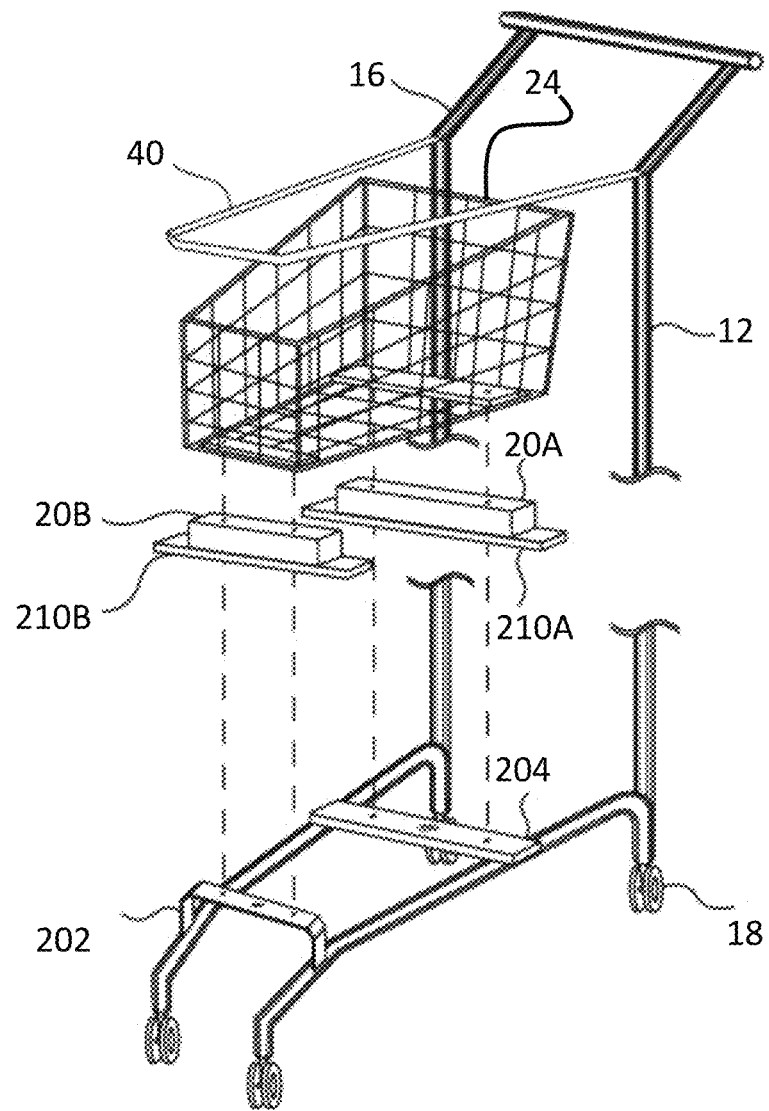
FIG. 8 is a schematic, exploded view of a shopping cart for autonomous payment, in accordance with embodiments of the present invention.

FIG. 8 shows a further depiction of an embodiment of the shopping cart of the present invention. Indicated, as in FIG. 1, are the upright portion 12 and the handle bar 16 of the shopping cart chassis, guard rail 40, as well as wheels 18. The scale 20 is indicated as including multiple pressure transducers, indicated as transducers 20A and 20B, which may be "load cells" attached to and directly below basket 24, such that the basket rests on the transducers. In some embodiments, a standard cart can be modified with one or more scale-leveling brackets, exemplified by scale-leveling brackets 202 and 204, in order to provide a level plane for the transducers. Shock absorbing pads 210A and 210B ("shock absorbers") may also be included. The shock absorbers may reduce the number of transducers required and thus reduce costs. Weighing of the products in basket 24 is not influenced by outside forces, such as a hindrance of movement of the basket or by a chassis support, the only point of contact being with the transducers. That is, the basket 24 is not directly attached to chassis 11.

The bracket structure may also distribute the weight of the basket and its contents to a single force sensor (pressure transducer), or in some embodiments to two force sensors (pressure transducers).

Because basket 24 is not attached directly to chassis 11, several sizes of baskets may be interchanged. Different brackets may compensate for different heights of baskets. Such design eases production whereby fewer, or ideally only one, chassis size is required to be produced.

In some embodiments, the connection between basket 26 and the transducers can be via a quick connect-disconnect fastener. As such, different sized brackets can be easily changed on chassis 11. A store may maintain a variety of sizes of brackets so that, for example, if many baskets of a particular size are in demand, the store, or perhaps the customers themselves, may assemble carts with baskets of the desired sizes. The same advantage could be realized at the manufacturing-assembly stage.

It should be understood that the above description is merely exemplary and that there are various embodiments of the present invention that may be devised, mutatis mutandis, and that the features described in the above-described embodiments, and those not described herein, may be used separately or in any suitable combination; and the invention can be devised in accordance with embodiments not necessarily described above.

The invention claimed is:

1. A shopping cart comprising:
   a cart chassis having an upright portion, a base, a handle bar attached to the upright portion, wherein wheels are operably attached to the base;
   a scale configured to rest on the base, wherein the scale is configured to provide an output signal indicative of a downward pressure on the scale, and wherein the scale comprises one or more weight transducers;
   a basket resting on the scale and connected to the base, wherein weights of products placed in the basket are indicated by the output signal of the scale;
   a user identification unit configured to receive a form of identification from a shopper and responsively to authenticate a shopper identification;
   one or more product sensors, configured to identify a product placed into the basket or a product placed in proximity to one of said sensors;
   a motion sensor, providing a motion signal to allow product weighing only when the shopping cart is stopped;
   a user interface comprising a touch screen, having an associated processor configured to receive a signal indicative of cart movement from the motion sensor and responsively to issue an alert that the product added to the basket cannot be weighed while the cart is in motion and that said product is to be removed and placed in the basket again when the cart is stopped, and further comprising a payment module configured to receive a payment method from the shopper and responsively to perform a payment transaction for the products in the basket.

2. The shopping cart of claim 1, wherein the motion sensor is one of an accelerometer, an encoder configured to measure wheel rotation, or a camera configured with movement recognition.

3. The shopping cart of claim 1, wherein said one or more product sensors comprise a barcode reader, an RFID reader, an NFC reader, or a QR.

4. The shopping cart of claim 1, wherein the user identification unit is a credit card reader, a smart card reader, a biometric reader, a mobile phone application or a mobile phone sensor.

5. The shopping cart of claim 1, wherein the payment module is configured to implement a payment transaction process according to a total price of products placed in the basket, to receive a payment transaction authorization, and responsively to issue a signal of a payment confirmation to confirm that payment has been successfully received.

6. The shopping cart of claim 5, wherein the payment transaction is one of a credit card transaction, a mobile phone application payment, or a bank transfer.

7. The shopping cart of claim 5, wherein the payment module further comprises a shopping cart registry and wherein the shopping cart registry is configured to log a "paid" status responsively to the payment confirmation.

8. The shopping cart of claim 5, wherein the payment module is further configured to transmit the shopping cart status to the user interface.

9. The shopping cart of claim 1, wherein the user interface further comprises a touch screen configured to accept a product identification identified by said one or more product sensors or entered by the shopper, and having an associated processor configured to determine a product correspondence between the product identification and the output signal of the scale.

10. The shopping cart of claim 9, wherein the user interface is further configured to provide product information comprising: cost of a product; price per weight of bulk products; nutrition information; product content weight; product volume; analogous products to a selected product; a notice of whether a product is on sale; product ingredients; and product warnings including potential allergens, gluten content, artificial sweeteners and colors.

11. The shopping cart of claim 9, wherein the product information is a type of bulk commodity and wherein the processor is further configured to determine a price according to the type of bulk commodity and the output signal of the scale.

12. The shopping cart of claim 11, wherein the type of commodity is one of a type of fruit, vegetable or nut.

13. The shopping cart of claim 9, wherein the processor is further configured to generate a lock release signal when a payment method is authenticated by the payment module and when a shopper is identified by the user identification unit.

14. The shopping cart of claim 9, further comprising a locking mechanism coupled to an external charger, wherein the locking mechanism is configured to receive power from the external charger to charge a power supply of the shopping cart, and the locking mechanism is further configured to receive a lock release signal from the user interface and responsively to release the shopping cart from the external charger.

15. The shopping cart of claim 1, further comprising a visual indicator on the shopping cart, wherein the visual indicator is configured to switch on responsively to the signal of payment confirmation.

16. The shopping cart of claim 1, further comprising an indoor navigation system configured to include a map and/or voice commands for in-store navigation.

17. The shopping cart of claim 1, wherein one or more of the user identification module, the payment module or the user interface are configured to receive input from a mobile phone.

* * * * *